United States Patent [19]
Ahne et al.

[11] Patent Number: 4,828,948
[45] Date of Patent: May 9, 1989

[54] METHOD FOR THE PRODUCTION OF HEAT-RESISTANT STRUCTURED LAYERS

[75] Inventors: Hellmut Ahne, Röttenbach; Winfried Plundrich, Kalchreuth, both of Fed. Rep. of Germany

[73] Assignee: Siemens Aktiengesellschaft, München, Fed. Rep. of Germany

[21] Appl. No.: 877,872

[22] Filed: Jun. 24, 1986

[30] Foreign Application Priority Data

Jun. 24, 1985 [DE] Fed. Rep. of Germany ....... 3522507

[51] Int. Cl.$^4$ .............................................. G03C 1/71
[52] U.S. Cl. ..................... 430/18; 430/284; 430/325; 430/296; 430/945; 522/96; 522/97; 427/53.1; 427/54.1
[58] Field of Search ................. 430/284, 325, 296, 18, 430/945; 522/96, 97; 427/53.1, 54.1

[56] References Cited

U.S. PATENT DOCUMENTS

| | | | |
|---|---|---|---|
| 3,694,415 | 9/1972 | Honda et al. | 522/97 |
| 3,776,889 | 12/1973 | Pande | 522/97 |
| 4,228,232 | 10/1980 | Rousseau | 430/284 X |
| 4,233,425 | 11/1980 | Hoffman | 525/455 |
| 4,246,391 | 1/1981 | Watson | 528/49 |
| 4,287,323 | 9/1981 | Cushman | 525/404 |
| 4,320,221 | 3/1982 | Tefertiller et al. | 528/69 |
| 4,436,806 | 3/1984 | Rendulic et al. | 430/284 X |
| 4,442,198 | 4/1984 | Tsao et al. | 430/284 X |

Primary Examiner—Paul R. Michl
Assistant Examiner—Cynthia Hamilton
Attorney, Agent, or Firm—Kenyon & Kenyon

[57] ABSTRACT

A cost-efficient method for producing dimensionally precise and high-grade heat-resistent structured layers by applying a single coating of a radiation-sensitive soluble polyether-based photopolymer in the form of a layer or foil on a substrate; irradiating the layer or foil through a negative with actinic light or by guiding a light, electron, laser, or ion beam; removing the nonirradiated layer or foil portions; and subsequent optional annealing, wherein the photopolymer comprises an addition product of an olefin-unsaturated monoisocyanate and a polether having at least one hydroxyl group. The layers provided according to the invention can withstand the thermal and mechanical stresses of dip soldering process, and protect circuit surfaces effectively and durably against moisture and corrosion; they are therefore suitable in particular as solder resist and insulating layers in microconductor technology.

21 Claims, No Drawings

METHOD FOR THE PRODUCTION OF HEAT-RESISTANT STRUCTURED LAYERS

FIELD OF INVENTION

This invention relates to a method for producing heat-resistant structured layers by applying radiation-sensitive soluble polymers in the form of a layer or foil on a substrate, irradiating the layer or foil through negatives with actinic light or by guiding a light, electron, laser or ion beam over the layer or foil, removing the nonirradiated portions of the layer or foil, and by optional subsequent tempering.

BACKGROUND OF THE INVENTION

Methods for the production of structured layers based on heat-resistant polymers are known, for example, from German Pat. No. 2 308 830 and from the European Patents 0 019 123 and 0 026 820. In these processes, soluble photoreactive precursors of highly heat resistant polymers are employed for photolithographic structuration, and in a subsequent tempering step the structures produced therefrom are cyclicized to highly heat resistant structures. For complete cyclization and removal of the cleavage products, temperatures up to 400° C. are needed. This requires substrates capable of high thermal load.

In circuit and transmission applications, e.g., in circuitboard technology, epoxy-based substrates which can be subjected to a thermal load of up to about 150° C. per hour and which can withstand temperatures of about 260° C. for a number of seconds in soldering processes are employed. The solder resists employed for partial conductor run coverings must meet similar thermal requirements; in order to cover the areas of the circuit surface which are not in contact with the solder metal, polymers of a medium thermal stability are needed. The epoxy and acrylate-based dry resists and screen printing lacquers which are still used for this purpose meet the requirements of a solder stop mask, yet these materials only partially fulfill the more stringent requirements for dimensional accuracy needed in micro-conductor technology with structures of less than 100 um, and at the stipulated cycle strength. For this, photolithographic lacquer systems are needed. There is already available a photostructurable epoxy-based lacquer system, which has chalcone groups incorporated in the polymer chain, and which provides sufficient dimensional accuracy. However, relatively long exposure and developing times are necessary for photostructuring. Moreover, the circuit system must often be protected from noxious gas; with the known lacquer system such protection can only be obtained by using costly multiple coatings. Because hardening times of several hours are required, the process is lengthy and expensive.

It is an object of the invention to provide a method for producing dimensionally exact, high-grade structured layers, for circuit surfaces in particular, which will withstand the extensive thermal and mechanical stresses of, for example, dip soldering, and which effectively and durably protect the circuit surface against moisture and corrosion with one coating process. It is another object to provide a method for producing structured layers, wherein the exposure, developing, and tempering times are shortened, so that the method is cost-efficient.

SUMMARY OF THE INVENTION

These and other objects are achieved by the method of the invention for producing a heat-resistant structured layer, which comprises applying a radiation-sensitive soluble polyether-based photopolymer in the form of a layer or foil on a substrate; irradiating a portion of the layer or foil through a negative pattern with actinic light or by guiding a light, electron, laser or ion beam over the layer or foil; and removing the nonirradiated portion of the layer or foil, wherein the photopolymer is an addition product of an olefin-unsaturated monoisocyanate and a polyether having at least one hydroxyl group.

The invention also provides a heat-resistant structured layer produced according to the method of the invention, which can be used in a wide variety of electrical applications.

DETAILED DESCRIPTION OF THE INVENTION

The method according to the invention provides for the inexpensive and efficient production of finely structured protective and insulating layers for semi-conductor and circuit applications, which effectively and durably protect the parts and circuits that are sensitive to corrosion. Especially advantageous is the fact that the developing process does not lead to undercutting; hence, solder bridges do not result from the soldering process. Also, the method according to the invention not only fulfills the dimensional accuracy requirements needed in connection with the structures produced, but it also permits a very high resolution in a wide range of layer thicknesses, with short developing times. The method is in particular cost-efficient because it produces, with a single application (with conventional equipment), and optionally after short tempering, highly, heat-resistant photostructured layers. Even under solder bath conditions, these layers remain dimensionally stable and fissureless, and are effective as a durable protection against moisture and corrosion. At the same time, good electrical characteristics are obtained which are not affected, even in a humid climate.

In the method according to the invention, the photopolymers can be employed advantageously together with light- or radiation-sensitive copolymerizable compounds. Such copolymerizable compounds are preferably compounds having acrylate and/or methacrylate groups, in particular trimethylol propane triacrylate and methacrylate, and/or 1,4-butanediol dimethacrylate. Alternatively, compounds containing allyl groups may be used, e.g., diallyl and triallyl cyanurates, as well as N-substituted maleinimides. In addition, photo initiators and/or sensitizers may be employed (cf.: "Industrie Chimique Belge," Vol. 24, 1959, pages 739 to 764; and J. Kosar, "Light-Sensitive Systems," John Wiley & Sons Inc., New York 1965, pages 143 to 146 and 160 to 188). Especially suitable are alpha-halogen acetophenones, dialkoxyacetophenones such as dimethoxy- and diethoxyacetophenone, benzoylphosphine oxides which may be substituted, and Michler's ketone. Benzoin ether; 4,4'-bis(diethylamino)benzophenone; 2,6-bis-(p-azidobenzylidene)-4-methylcyclohexanone; thioxanthones such as isopropyl thioxanthone; and acetophenone also are suitable as photo initiators or sensitizers. Bonding aids may also be used advantageously in the method of the invention. These are preferably silanes, such as vinyltriethoxysilane, vinyltris(beta-methoxyethoxy)silane, gamma-methacryloxypropyltrimethoxysilane, gamma-glycidoxypropyltrimethoxysilane and gamma-aminopropyltriethoxysilane.

The photopolymers employed in the method of the invention are described in the co-pending U.S. patent application "Polyether-based Photopolymers", U.S. Ser. No. 878,020. These photopolymers generally have the following structure:

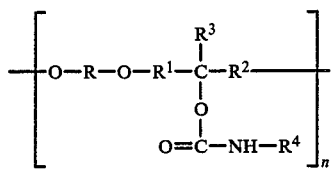

where $n \geq 50$.

For R, $R^1$, $R^2$, $R^3$ and $R^4$ the following applies:

R is an optionally halogenated, divalent, i.e. difunctional radical, of aromatic and/or aliphatic and/or cycloaliphatic structure, optionally with hetero atoms, and/or of heterocyclic structure;

$R^1$ is a divalent aliphatic radical;

$R^2$ is an optionally halogenated, divalent aliphatic and/or cycloaliphatic radical;

$R^3$ is hydrogen or an optionally halogenated alkyl group;

$R^4$ is an olefin unsaturated group bound through an aliphatic and/or cycloaliphatic and/or aromatic bond, for example, a group containing alkyl ether or maleinimide, or preferably an optionally substituted (meth)acrylester-containing group.

Preferred photopolymers are addition products of isocyanatoethyl methacrylate and phenoxy resins, optionally having fluorinated ispropyl groups, or addition products of phenoxy resins and olefin-unsaturated monisocyanates in the form of addition products of 2,4-diisocyanatotoluene and hydroxyethyl acrylate or methacrylate. Such photopolymers are illustrated in the following exemplary formulas:

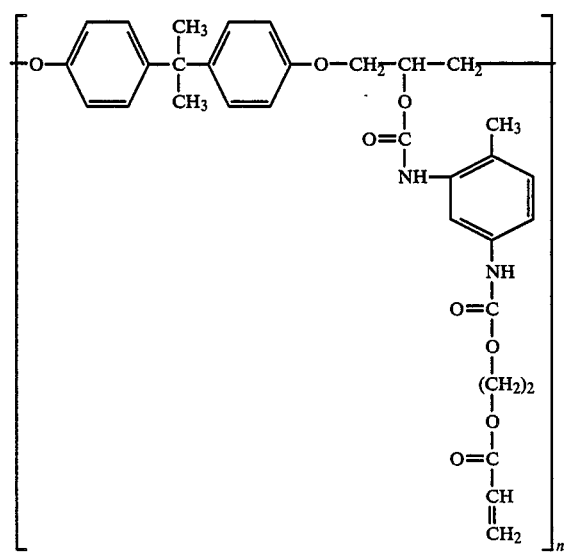

-continued

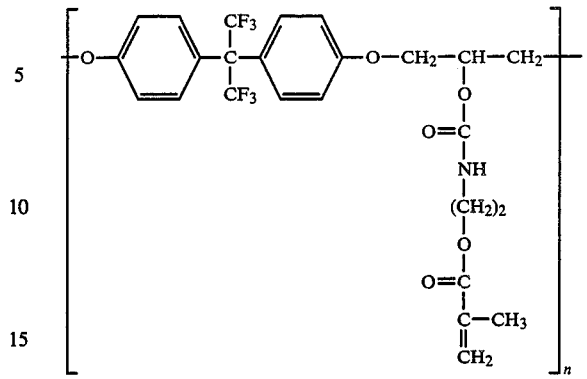

As mentioned above, the structured layers are produced according to the invention by applying the photopolymer in the form of a layer or foil on a substrate, and exposing it to actinic light through a mask, or irradiating it by guiding a light, electron, laser, or ion beam. Thereafter, the unexposed or nonirradiated layer or foil portions are dissolved or pulled off, and the resulting structured layers or relief structures are optionally tempered. Preferably, the photopolymer is applied on the substrate dissolved in a conventional organic solvent such as cyclohexanone, gammabutyrolactone, N-methylpyrrolidone and mixtures thereof. The concentration of the photo resist solution can be adjusted so that with known coating methods, such as centrifuging, dipping, spraying, pouring, knifing, brushing or rolling, layer thicknesses of 0.01 to about 500 μm can be produced. To obtain a uniform and good surface quality on substrates having smooth surfaces, pouring (see, European Pat. No. 0 002 040) knifing, and in particular, electrostatic spray coating and centrifugal coating at 300 to 10,000 revolutions per minute are preferred. On uneven surfaces, such as circuit boards with copper conductors on the surface, centrifugal speeds of 300 to 1500 are preferred. The viscosity range of the lacquer solutions used in knifing, spraying, and pouring is preferably between 200 and 1500 mPa.s at 23° C.

The photo resist layer applied on the substrate, which consists preferably of circuitboard material, glass, metal, plastic or semiconductors, can be separated from the solvent at room temperature, preferably at temperatures of 50° to 80° C., in circulating nitrogen or air; the operation may take place under vacuum, or drying may be done with infrared lamps or a heated plate.

To obtain an acceptable solubility difference between the irradiated and the nonirradiated layer or foil portions, when using a 350 W superpressure mercury lamp in connection with the method of the invention, exposure times between 5 and 400 s are sufficient depending on the composition and on the layer thickness. After exposure, and an optional second drying process the unexposed portions are dissolved out with organic solvents.

The structured layers or relief structures produced by the method of the invention exhibit outstanding edge sharpness, high resolution, and have fissureless homogeneous surfaces and dimensional stabilitis which withstand the thermal and mechanical strains of dip soldering processes. The adhesion on the solder is very low, so that, as desired, no solder beads stick to the polymer layer. The structured layers produced according to the invention are elastic enough to pass cycle tests between −65° and +125° C. without fissuration. Circuit surfaces covered with the structured layers show no conductor corrosion in climate tests at 40° C., 92% relative humidity, and a voltage of 100 V. Such layers are suitable not only as solder resist masks; they can also be employed as effective and durable protective layers against the action of moisture and noxious gases.

The high-purity structured layers produced according to the invention are also suitable for the production of passivation layers on semi-conductor components, thin and thick film circuits, solder protection layers on multi-layer wirings, and insulating layers which are components of film circuits. The layers can also be used as miniaturized protective and insulating layers on electrically conducting, semi-conducting, and/or insulating base materials. Additionally, the layers can be used generally for the fine structuring of substrates, and for structure transfer processes, such as wet or dry etching processes, wattless or electroplating metal deposition and vapor deposition methods, and also as masks for ion implantation; the layers provide intermediate protection when used with such processes. Moreover these layers are suitable as insulating and protective layers in electrical engineering and in micro-electronics, as damping substances for surface wave filters (in particular, television intermediate frequency filters), as alpha-ray protectors on the cell fields of memory components, and as orientation layers in liquid crystal displays.

The invention will be further described by reference to the following examples which are not intended to be limiting but rather illustrative of the invention. The examples may of course be varied in accordance with the spirit and scope of this description.

EXAMPLE 1

40 parts pure 2,4-diisocyanatotoluene are added dropwise to 69 parts (by weight) dried dichloromethane in the absence of moisture. 29.2 parts 2-hydroxyethyl acrylate are then slowly added dropwise at room temperature under agitation to the solution thereby obtained. After standing for 24 hours, the conversion of the isocyanate groups is determined to be 99% by titration. The photo-reactive isocyanate is then extracted from the reaction solution with 250 parts by weight light petrol. After removal of the extraction medium, it is isolated as a clear viscous liquid, with a yield of 64.5 g, or 93% of the theoretical value.

At room temperature and under agitation, 140 parts dry gamma-butyrolactone, 137 parts dry N-methyl pyrrolidone, 50 parts of the pure photo-reactive monoisocyanate isolated in the above described manner, and 0.1 parts dibutyl tin dilaurate are added to 35 parts of the phenoxy resin Rütapox 0717 ("Rütapox" is a trademark of Rütgerswerke AG). After stirring the reaction solution for 48 hours, 7 parts by weight ethanol are added. After another 24 hours, isocyanate groups are no longer detectable.

0.65 part benzoin isopropyl ether, 0.08 parts Michler's ketone, 1.65 parts trimethylol propane triacrylate, and 0.3 parts vinyl-tris(beta-methoxyethoxy)silane are then added to 100 parts of the photo-reactive phenoxy resin produced in the manner described above (as a 23% resin solution). The solution is then pressure filtered through a 5 μm filter. The viscosity of the resulting solution is 830 mPa.s at 23° C.

By centrifuging the solution at 800 rpm onto a silicon disk coated with a bonding aid, followed by drying for 30 minutes at 60° C. in a circulating air oven, 23 μm thick homogeneous layers are obtained. After exposure for 40 s through a mask with a 350 W superpressure mercury lamp, the layers are developed with gamma-butyrolactone/xylene (volumetric ratio 1:2) and then rinsed with xylene in a spraying process to produce structured layers having sharp contours. The edge formations and the surface qualities of these layers are not impaired by tempering for one hour at 150° C. The resolution quality of the pattern is ≦20 μm.

A photo-structured layer produced as described above and treated with known commercial fluxes exhibits a homogeneous fissureless surface after being tested in a solder bath at 260° C. with an immersion time of 20 s. The solder runs off the lacquer surface in beads.

EXAMPLE 2

33 parts pure isocyanatoethyl methacrylate and 0.1 parts dibutyl tin dilaurate are added to a solution of 110 parts Rutapox 0723 (50% solution in cyclohexanone/ethylglycol acetate) in 114 parts gamma-butyrolactone. The mixture is then stirred for 30 hours at room temperature. Thereafter, 9 parts 2-hydroxyethyl methacrylate are added to the reaction solution. After another 24 hours, 0.6 parts dichloroacetophenone, 0.3 parts diethoxyacetophenone, 0.3 parts Michler's ketone and 0.3 parts vinyl-tris-(beta-methoxyethoxy)silane are added to 100 parts of the resin solution. Subsequently, the solution is pressure-filtered through a 5 μm filter.

The filtered solution of the photo-reactive phenoxy resin is centrifuged at 400 rpm onto a circuitboard test plate with copper conductors on the surface, and then dried in a circulating air oven for ½ hour at 70° C. The thickness of the resulting lacquer film is then 50 μm. Next, the film is exposed with a 350 W superpressure mercury lamp through a mask for 10 s and subjected to a 30 minutes final drying at 70° C. in a circulating air oven. After developing for 35 s with cyclohexanone, using water as a quencher, sharp-edged structured layers, whose surface qualities are not impaired even by 100 cycles between −65° and +125° C., are obtained. These layers withstand both undamaged flow and dip soldering processes at 260° C.; the solder runs off the surface in beads. Moisture tests at 40° C., 92% relative humidity, and a voltage of 100 V reveal no corrosion in the conductor areas covered with lacquer.

EXAMPLE 3

62 parts 2,4-diisocyanatotoluene are added in the absence of moisture to 113.2 parts dried dichloromethane. Thereafter, at room temperature and with agitation, 51.2 parts 2-hydroxyethyl methacrylate are slowly added in drops. After a reaction time of 24 hours at room temperature, the isocyanate conversion is determined titrimetically to be 99%. Upon addition of 450 parts light petrol, a precipitate of white crystals is obtained. The yield of pure photo-reactive monoisocyanate is 105 parts, or 93% of the theoretical value.

125.2 parts phenoxy resin solution (Rütapox 0723) are added, in the absence of moisture, to a solution of 95 parts of the photo-reactive monoisocyanate produced in the manner described above, which is in a mixture of 140 parts gammabutyrolactone, 105 parts N-methyl pyrrolidone and 0.01 parts dibutyl tin dilaurate. Reaction is allowed to proceed under agitation for 12 hours at 50° C. Thereafter, 8 parts 2-hydroxyethyl methacrylate are added to the reaction solution at this temperature. After an additional 5 hours, 4 parts ethanol are added. After 24 hours the resin solution has a viscosity of 330 mPa.s at 23° C.

0.66 parrs isopropyl thioxanthone, 0.08 parts Michler's ketone, 1.65 parts trimethylol propane triacrylate and 0.3 parts vinyltriethoxysilane are added to 100 parts of the solution described above. The mixture is then filtered through a 5 μm filter at a pressure of 5 bars and poured on substrates to produce 20 μm thick lacquer layers. The layers are irradiated with a 350 W superpressure mercury lamp for 30 s through a mask. Thereafter, the exposed layer is redried in a circulating air oven for 5 min at 90° C. The structuration (time: 10 s) occurs by means of a developer mixture of gamma-butyrolactone and xylene (volumetric ratio 1:2), quenching being done with xylene. The structural layer produced in this manner is resistant to solder bath.

EXAMPLE 4

A mixture of 23.6 parts pure 2-hydroxyethyl acrylate and 24.8 parts pure 2-hydroxyethyl methacrylate is slowly added in drops at room temperature under agitation and in the absence of moisture, to a solution of 66.8 parts pure 2,4-diisocyanatotoluene in 115.3 parts dichloromethane. After reaction at room temperature for 40 hours, the isocyanate conversion is determined to be 98% by titration.

The resulting solution of the photo-reactive monoisocyanate is combined with a solution of 107 parts Rutapox 0717 in 397 parts gamma-butyrolactone and with 0.22 parts dibutyl tin dilaurate. After reaction at room temperature for 25 hours, 15 parts ethanol are added to the reaction solution. After another 24 hours, the solution is ready to be used for coatings.

To 100 parts of the polyether solution produced in the manner described there are added 1.2 parts 2,4,6-trimethyl benzoylphosphine oxide, 0.3 parts Michler's ketone and 0.3 parts vinyltriethoxysilane. The mixture is filtered through a 5 μm filter at a pressure of 5 bars and then poured on copper substrates to produce 30 μm thick lacquer layers. The layers are irradiated through a mask for 30 s with a 350 W superpressure mercury lamp. After developing according to Example 2 for 35 s, structures with a smooth fissureless surface, which are stable under solder bath conditions even at 260° C. are obtained. The solder does not adhere to the lacquer surface, but runs off in beads.

This invention has been described in terms of specific embodiments set forth in detail, but it should be understood that these are by way of illustration only, and that the invention is not necessarily limited thereto. Modifications and variations will be apparent from this disclosure and may be resorted to without departing from the spirit of this invention, as those skilled in the art will readily understand. Accordingly, such variations and modifications are considered to be within the scope of this invention and the following claims.

What is claimed is:

1. A method for the production of a heat-resistant layer which comprises applying a radiation-sensitive mixture of a soluble polyether-based photopolymer and a copolymerizable compound in the form of a layer or foil on a substrate; irradiating a portion of the layer of foil through a negative pattern with actinic light or by guiding a light, electron, laser or ion beam over the layer or foil; and removing the nonirradiated portion of the layer or foil; wherein the photopolymer is an addition product of an olefin-unsaturated monoisocyanate and a phenoxy resin and the copolymerizable compound contains an acrylate or methacrylate group.

2. A method according to claim 1, further comprising the step of tempering by heating after removing the nonirradiated portion of the layer or foil.

3. A method according to claim 1, wherein the photopolymer is employed together with a photo initiatior or photo sensitizer.

4. A method according to claim 3, wherein the photo initiator or photo sensitizer is selected from the group consisting of alpha-halogen acetophenone, dialkoxyacetophenone, benzoylphosphine oxide, and Michler's ketone.

5. A method according to claim 1, wherein the phenoxy resin has a molecular weight of between 15,000 and 30,000.

6. A method according to claim 1, wherein the olefin-unsaturated monoisocyanate is an isocyanate selected from the group consisting of an isocyanate having a methacrylate group, and the addition product of hydroxyethyl acrylate or methacrylate, and 2,4-diisocyanotoluene.

7. A heat-resistant structured layer, produced according to claim 1.

8. A method for the production of a heat-resistant structured layer which comprises applying a radiation-sensitive soluble polyether-based photopolymer in the form of a layer or foil on a substrate; irradiating a portion of the layer or foil through a negative pattern with actinic light or by guiding a light, electron, laser or ion beam over the layer of foil; and removing the nonirradiated portion of the layer or foil; wherein the photopolymer is an addition product of an oelfin-unsaturated monoisocyanate and a phenoxy resin and said olefin-unsaturated monoisocyanate is selected from the group consisting of an isocyanate having a methacrylate group, and the addition product of hydroxyethyl acrylate or methacrylate, and 2,4-diisocyanatotoluene.

9. A heat-resistant structured layer produced according to claim 8.

10. A heat resistant structured layer of claim 9 wherein the substrate is a structure transfer support, the irradiated layer or foil is a resist with an intermediate protective function and the heat resistant structure layer is used in a structure transfer process.

11. A heat resistant structure layer of claim 9 wherein the substrate is a semiconductor material and the irradiated layer or foil is a protective and insulating material.

12. A heat resistant structure layer of claim 9 wherein the substrate is a surface wave filter support and the irradiated layer or foil is a damping substrate.

13. A heat resistant structured layer of claim 9 wherein the substrate is a memory component containing cell fields and the irradiated layer or foil is an alpha-ray protecting means.

14. A heat resistant structured layer of claim 9 wherein the substrate is a liquid crystal display and the irradiated layer or foil is an orientation layer.

15. A heat-resistant structured layer of claim 9 wherein the substrate is a micro-conductor board and the irradiated layer or foil is a durable, protective solder resist and insulating layer.

16. A method according to claim 8, further comprising the step of tempering by heating after removing the nonirradiated portion of the layer or foil.

17. A method according to claim 8, wherein the photopolymer is employed together with a light-or radiation-sensitive copolymerizable compound.

18. A method according to claim 17, wherein the copolymerizable compound contains an acrylate or methacrylate group.

19. A method according to claim 8, wherein the photopolymer is employed together with a photo initiator or photo sensitizer.

20. A method according to claim 19, wherein the photo initiator or photo sensitizer is selected from the group consisting of alpha-halogen acetophenone, dialkoxyacetophenone, benzoylphosphine oxide, and Michler's ketone.

21. A method according to claim 8, wherein the phenoxy resin has a molecular weight of between 15,000 and 30,000.

* * * * *